(12) United States Patent
Schubert et al.

(10) Patent No.: US 6,822,929 B1
(45) Date of Patent: Nov. 23, 2004

(54) MICRO ACOUSTIC SPECTRUM ANALYZER

(75) Inventors: W. Kent Schubert, Albuquerque, NM (US); Michael A. Butler, Andover, MA (US); Douglas R. Adkins, Albuquerque, NM (US); Larry F. Anderson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/606,526

(22) Filed: Jun. 25, 2003

(51) Int. Cl.$^7$ .................. G01N 33/00; H04R 23/00
(52) U.S. Cl. .................. 367/181; 73/659; 367/176
(58) Field of Search .................. 73/649, 659, 584; 367/176, 181, 178

(56) References Cited

U.S. PATENT DOCUMENTS

| | | | |
|---|---|---|---|
| 5,640,133 A | 6/1997 | MacDonald et al. | |
| 5,729,075 A | 3/1998 | Strain | |
| 5,836,203 A | 11/1998 | Martin et al. | |
| 6,012,334 A | * 1/2000 | Ando et al. | 73/651 |
| 6,227,054 B1 | * 5/2001 | Ando et al. | 73/651 |
| 6,236,281 B1 | 5/2001 | Nguyen et al. | |
| 6,404,304 B1 | 6/2002 | Kwon et al. | |
| 6,455,980 B1 | * 9/2002 | Bernstein | 310/324 |

OTHER PUBLICATIONS

Adkins et al., "Microfabricated Teeter–Totter Resonator", patent application No. 10/436,597, filed May 12, 2003.
Stafford et al., "Multi–Tunable Microelectromechanical System Resonator", patent application No. 10/443,951, filed May, 21, 2003.
Martin et al., "Flexural plate wave resonator excited with Lorentz forces," *J. Appl. Phys.* 83(9), 4589 (1998).
M. Elwenspoek and R. Wiegerink, *Mechanical Microsystems*, Springer–Verlag, pp. 209–228 (2001).
Givens et al., "A high sensitivity, wide dynamic range magnetometer designed on a xylophone resonator," *Appl. Phys. Lett.* 69(18), 2755 (1996).
Wickenden et al., "Micromachined polysilicon resonating xylophone bar magnetometer," *Acta Astronautica* 52, 421 (2003).
J. Pope, "Chapter 107: Analyzers," *Handbook of Acoustics*, Malcolm J. Crocker, ed. John Wiley & Sons, Inc (1998).

* cited by examiner

*Primary Examiner*—Ian J. Lobo
(74) *Attorney, Agent, or Firm*—Kevin W. Bieg

(57) ABSTRACT

A micro acoustic spectrum analyzer for determining the frequency components of a fluctuating sound signal comprises a microphone to pick up the fluctuating sound signal and produce an alternating current electrical signal; at least one microfabricated resonator, each resonator having a different resonant frequency, that vibrate in response to the alternating current electrical signal; and at least one detector to detect the vibration of the microfabricated resonators. The micro acoustic spectrum analyzer can further comprise a mixer to mix a reference signal with the alternating current electrical signal from the microphone to shift the frequency spectrum to a frequency range that is a better matched to the resonant frequencies of the microfabricated resonators. The micro acoustic spectrum analyzer can be designed specifically for portability, size, cost, accuracy, speed, power requirements, and use in a harsh environment. The micro acoustic spectrum analyzer is particularly suited for applications where size, accessibility, and power requirements are limited, such as the monitoring of industrial equipment and processes, detection of security intrusions, or evaluation of military threats.

14 Claims, 10 Drawing Sheets

MICRO ACOUSTIC SPECTRUM ANALYZER

CROSS-REFERENCE TO RELATED APPLICATIONS

This application is related to the co-pending and commonly owned U.S. patent application Ser. No. 10/443,951, filed May 21, 2003, and U.S. patent application Ser. No. 10/436,597, filed May 12, 2003, which are both incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to acoustic spectrum analysis and, in particular, to a micro acoustic spectrum analyzer that uses one or more microfabricated resonator filters to provide frequency analysis of a sound signal.

BACKGROUND OF THE INVENTION

Acoustic spectrum analysis involves decomposing an input spectrum into different frequency components as a function of time. To be useful, the relative sound intensities (i.e., the rate of sound energy transmission per unit area) in the different frequency ranges must be determined also. Therefore, an acoustic spectrum analyzer provides the level of a sound signal as a function of frequency.

The analysis of sound in various frequency bands can be a valuable means to monitor industrial equipment and processes, detect security intrusions, or evaluate military threats. Such analysis can be provided by a sensor comprising an acoustic spectrum analyzer. In an industrial setting, the sensor could be used to diagnose machine health by comparing the sound emitted by a defective machine to the normal operating spectrum, or by picking up a characteristic sound that might be emitted by a worn bearing or belt. The sensor could also be used for access control, by recognizing a spoken word or phrase; or an alarm system, by recognizing characteristic sounds, like broken glass or a turning lock mechanism. In a military setting, the sensor could be used to recognize characteristic sounds of particular military vehicles in the air, on the land, or at sea.

In addition, there is a growing recognition that a large array of simple acoustic sensors may have advantages over a small array of more sophisticated sensors. For example, often the signal that clearly identifies a military or security threat is rapidly attenuated with distance. This is particularly true for pressure radiation sources at frequencies above the audio range. A simple sensor in close proximity to the threat could provide the best identification of the source. An array of such strategically located, miniaturized sensors could be used to monitor a large building or battlefield.

The standard approach to acoustic spectrum analysis is to use digital signal processing (DSP) to analyze the spectrum picked up and recorded by a microphone and recording system. DSP typically uses fast Fourier transform (FFT) methodology to quickly translate time-domain signals and provide a frequency-domain spectrum. However, DSP with an FFT analyzer requires extensive signal processing and considerable computing power to analyze the massive amounts of data acquired, which implies large physical size and power requirements. Because acoustic signals are by their nature nonstationary, this is particularly the case with real-time analysis. For example, current speech recognition systems require the computing power and data processing capabilities of a state of the art personal computer. Furthermore, if the computing power is remote from the sound source, the data communication overhead can be enormous. Even with the advances in modern radio frequency communications and computing technologies, it is not possible to do acoustic spectrum analysis in a truly miniature, low-power system. Therefore, in certain applications the power and size overhead of DSP make it impractical.

Alternatively, a simple acoustic spectrum analyzer can comprise one or more filters combined with a sound level meter. A real-time acoustic spectrum analyzer based on this approach relies on a bank of bandpass filters that pass selective frequencies, enabling the signal to be evaluated over a set of frequency bands simultaneously. Filters thereby enable the real-time frequency analysis of nonstationary signals and the more rapid analysis of stationary signals. FFT techniques can be used in combination with the filter set to extend the capabilities of the simple filter bank analyzer.

However, there remains a need for a low-power, low-cost, small-sized acoustic spectrum analyzer that can be used in applications were size, accessibility, and power availability are limited. The present invention provides a microfabricated acoustic spectrum analyzer that can fulfill this need in a low-power, miniature system. The micro acoustic spectrum analyzer combines novel microfabricated resonator technologies with state-of-the art signal processing and microphone technology to provide spectral analysis on a chip. The micro acoustic spectrum analyzer reduces the amount of data to be processed and exfiltrated through the use of selective resonant filtering of the input signal. Therefore, by doing the data analysis on-chip, much of the computational and data communication load of DSP is eliminated. The micro acoustic spectrum analyzer can be designed specifically for portability, size, cost, accuracy, speed, power requirements, use in a harsh environment, or whatever the application calls for.

In its simplest form, the micro acoustic spectrum analyzer of the present invention comprises a limited set of microfabricated resonators to provide signal analysis tailored to a specific application so that it "listens" selectively in the frequency bands of particular interest. This simple micro acoustic spectrum analyzer does not provide a full-blown, wide-band, high-resolution acoustic spectrum analysis system capable of recognizing any arbitrary sound. However, by recording and analyzing only the data of interest, the simple micro acoustic spectrum analyzer can dramatically reduce the data communication and processing overhead required to recognize a target sound, voice, or word. This targeted capability enables a significant reduction in size and power requirements that could be used in situations that preclude a full-blown analysis system. For example, the small size, low power, low cost of the on-chip acoustic spectrum analysis technology enables deployment of one or more sensors near the sound source. The sensor could then act as an intelligent input, or prefilter, to a remote, more capable digital signal processing system. With a sufficient number of resonator filters, the micro acoustic spectrum analyzer can provide analysis of a sound having a broader frequency range. This more sophisticated micro acoustic spectrum analyzer can be used for speech analysis and recognition, for example.

SUMMARY OF THE INVENTION

The present invention is directed to a micro acoustic spectrum analyzer for determining the frequency components of a fluctuating sound signal comprising a microphone to pick up the fluctuating sound signal and produce an alternating current electrical signal; at least one microfabricated resonator, each resonator having a different resonant frequency, that vibrate in response to the alternating current electrical signal; and at least one detector to detect the vibration of the at least one microfabricated resonator. The micro acoustic spectrum analyzer can further comprise a mixer to mix a reference signal with the alternating current electrical signal from the microphone to shift the frequency spectrum to a frequency range that is a better matched to the resonant frequencies of the at least one microfabricated resonator. The invention can further comprise a means for scanning and storing the detected vibrations and a pattern recognition processor to compare the detected vibrations to a library of profiles.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
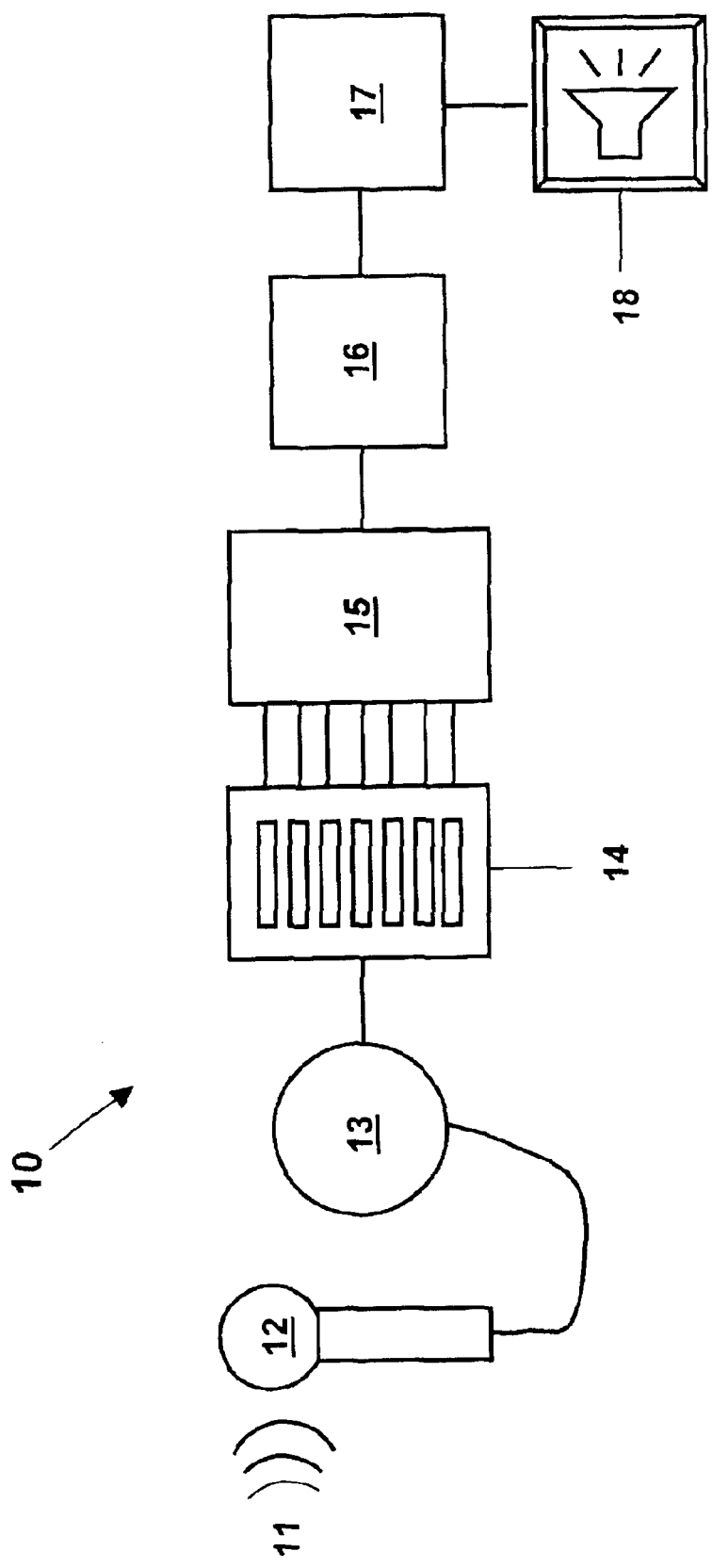
FIG. 1 shows a block diagram of the micro acoustic spectrum analyzer.

In FIG. 1 is shown a block diagram of an embodiment of the micro acoustic spectrum analyzer 10 of the present invention. The micro acoustic spectrum analyzer 10 comprises a microphone 12 to pick up "target" sound waves 11 and produce an alternating current electrical signal that drives at least one microfabricated resonator 14. Each resonator 14 can have a different natural vibration, or resonant frequency. The micro acoustic spectrum analyzer 10 can further comprise a mixer 13 that shifts the input frequency spectrum of the microphone electrical signal to a shifted frequency range that is a better matched to the natural vibration frequencies of the microfabricated resonators 14. At least one detector 15 can be used to detect the resulting vibrations from the at least one resonator 14. If more than one resonator 14 is used, the micro acoustic spectrum analyzer 10 can further comprise a storage/scanning device 16 to store and scan the detector outputs and read out the scanned detector signals. A pattern recognition processor 17 can be used to compare the sound level versus frequency of the detected vibrational signals against a library of profiles. An alarm 18 can sound if the scanned signal displays a signature that matches a known profile.

The electroacoustic microphone 12 picks up the acoustic signal 11 from the target and produces an electrical signal proportional to the sound pressure. The microphone 12 preferably has a high sensitivity (i.e., output voltage/sound pressure), low noise level, and wide dynamic range. Use of the microphone 12 also permits the sound propagation media to be separated from the ambient environment of the resonator 14. Therefore, the resonators 14 can be located in an inert atmosphere or vacuum to protect the microfabricated components, while a microphone or hydrophone can be selected for air or water sound propagation media.

The resonators 14 can be selected to "listen" in the frequency bands that are chosen to sample critical segments of the known acoustic spectrum of the target. Therefore, the number, resonant frequency, and bandwidth of the resonators 14 can be selected to recognize the target sound. Sounds that emanate from speech or machinery are typically composed of multiple tones. By selecting resonators 14 that match the tonal pattern of a target of interest, a signal is generated by each resonator when the selected tone is encountered. A microprocessor or simple comparator electronics can be used to monitor the resonator signals and produce an alarm signal when the sequence of interest is encountered.

For the resonators to listen in the audio frequency range (100 Hz to 20 kHz), and particularly in the lower part of the range that characterizes human speech, the size of matched resonators (i.e., on the order of centimeters) precludes incorporation of an array of such large resonators on a single substrate with sub-centimeter dimensions. This is because the natural frequency of a resonant element increases as the size of the mechanical element shrinks. In particular, as the resonant frequency increases beyond the audible range, the acoustic mismatch between a microfabricated resonator and an incident sound wave worsens. Therefore, the sensitivity of the resonant element to the incident sound wave progressively worsens as the device size shrinks. For example, mechanical resonators with dimensions of less than 1 millimeter typically have resonant frequencies greater than about 20 kHz, regardless of whether they are based on resonant beams, plates, or membranes. At frequencies above or below resonance, they would not have the sensitivity required to pick up the target signals or the narrow bandwidth required for spectrum analysis with sufficient resolution to detect a unique sound signature.

Figure 2:
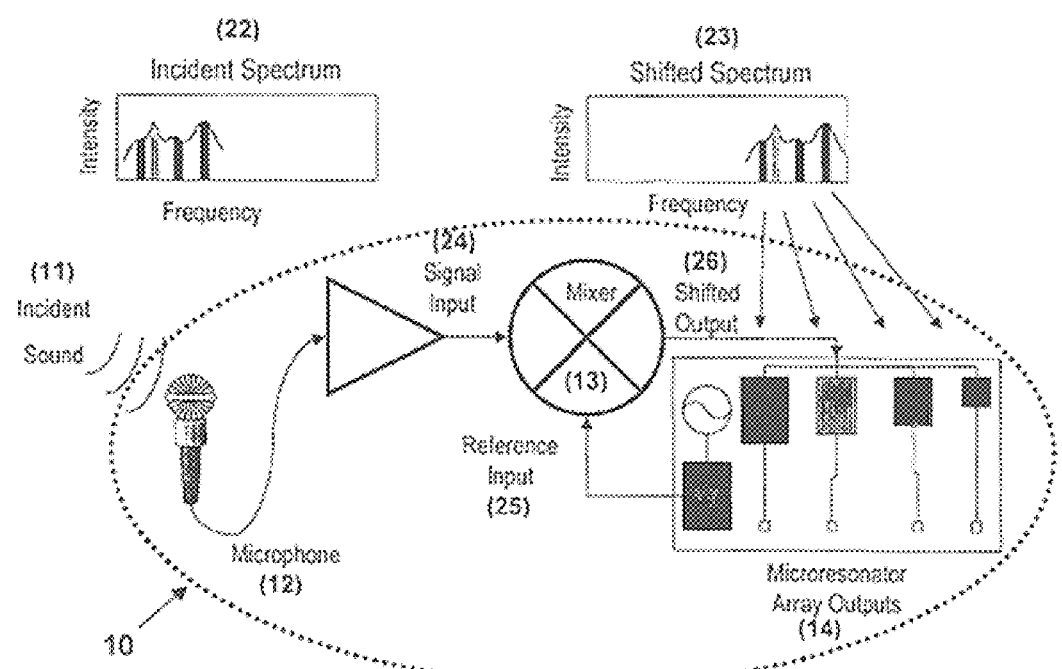
FIG. 2 shows a schematic illustration of a mixer for shifting the input frequency spectrum to a higher frequency shifted spectrum.

Therefore, as illustrated schematically in FIG. 2, the micro acoustic spectrum analyzer 10 of the present invention can further comprise a mixer 13 that shifts the input spectrum 22 to provide a shifted spectrum 23 having an ultrasonic frequency range that is better matched to the natural vibration frequencies of the microfabricated resonators 14. This spectrum shifting is accomplished by mixing the microphone alternating current electrical output 24 with a higher frequency reference signal 25 that can be generated by an on-chip waveform generator 27. Since the resonators 14 do not have to pick up the acoustic signal directly (the resonators 14 are driven by the frequency-shifted microphone signal 26), they can be reduced in size and vacuum packaged for improved sensitivity and ruggedness. By using the miniature microphone 12, the frequency shifting mixer 13, and resonantly driven resonators 14, the micro acoustic spectrum analyzer 10 can have a large dynamic range.

For example, by mixing an input spectrum that ranges from 100 HZ to 8 kHz with a reference signal at 50 kHz, the entire spectrum is shifted so that the shifted spectrum spans from 50.1 kHz to 58 kHz. An array of eight resonators spanning this frequency range can easily fit on an electronic chip a few millimeters on a side. Depending on the application, the resonators can be tuned to particular bands of the shifted spectrum.

High fidelity spectrum analysis with the same bandwidth at higher frequencies requires high-Q resonators. For example, 50 Hz bandwidth at 50 kHz indicates a Q of 1000. However, the higher Q's may require a slower sampling rate to maintain resolution. Therefore, it is preferable to optimize the resonator bandwidth for sensitivity, spectral resolution, and sampling rate to achieve analysis accuracy.

The unshifted or frequency-shifted microphone electrical signal can drive one or more resonators. A microelectromechanical resonator comprises a vibrating element of a certain shape. Depending on the shape, the resonator can support several types of vibrations, e.g., longitudinal, transverse, torsional, and lateral, that can support a number of vibrational modes or resonances. The stress, mass, or shape of the resonator is typically designed such that one of these modes dominates and the resonant frequency of the dominant mode is matched to the driving excitation signal. Furthermore, a high mechanical quality factor, Q, requires that losses to the surrounding medium and support mounting and intrinsic damping due to energy losses to the resonator material are low.

There are a variety of resonator technologies based on diaphragm or beam structures that are compatible with silicon-based microelectronics and are suitable for the micro acoustic spectrum analyzer of the present invention. Such resonators can operate on electrostatic, magnetic, piezoelectric, electrothermal, optothermal, or dielectric actuation mechanisms. See, e.g., M. Elwenspoek and R. Wiegerink, *Mechanical Microsensors*, Springer-Verlag, pp. 209–228 (2001). Resonators that operate on magnetic actuation principles are particularly attractive for use with micro acoustic spectrum analyzer, because of their low drive voltages. These rely on a Lorentz force generated by an alternating electrical current flowing in the resonator interacting with an external magnetic field to excite a mechanical vibration in the structure. These electromagnetic resonators include flexural plate wave (FPW) resonators, xylophone, and teeter-totter resonators.

Figure 3:
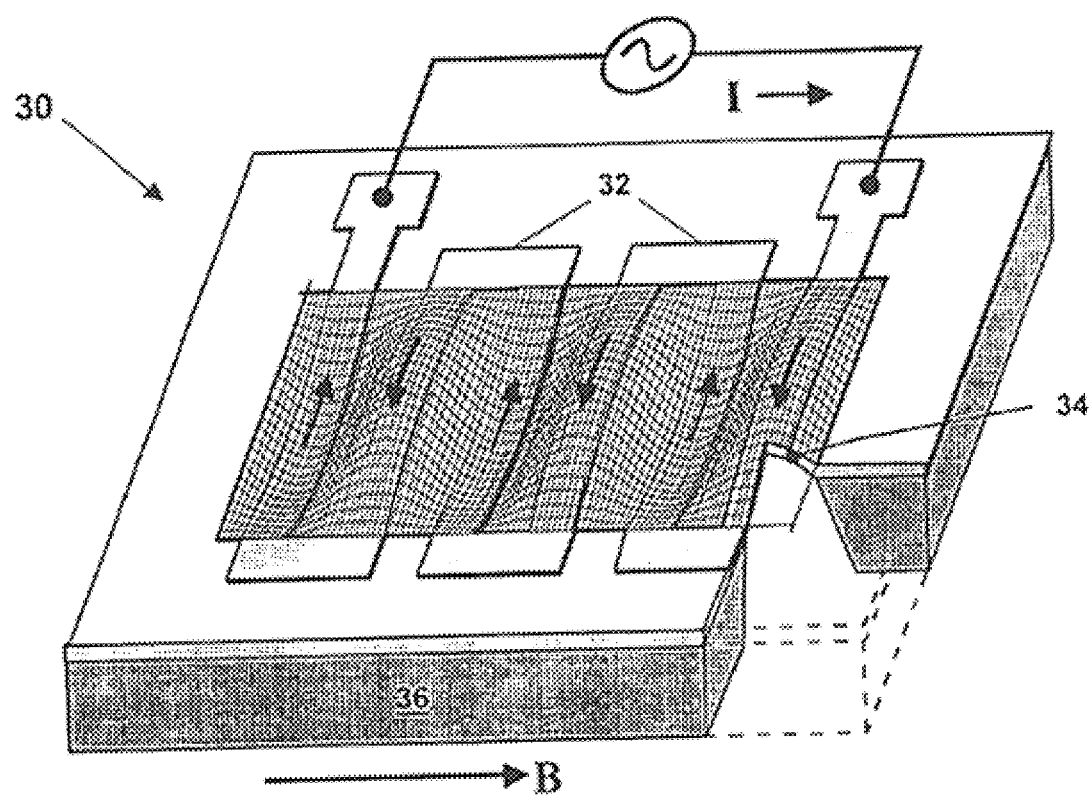
FIG. 3 shows a magnetically excited flexural plate wave (mag-FPW) resonator.

A magnetically excited FPW (mag-FPW) resonator is described in S. J. Martin et al., "Flexural plate wave resonator excited with Lorentz forces," *J. Appl. Phys.* 83(9), 4589 (1998) and U.S. Pat. No. 5,836,203 to Martin et al., which are incorporated herein by reference. In FIG. 3 is shown the mag-FPW resonator 30 of Martin et al. This mag-FPW resonator 30 comprises current conductor lines 32 patterned on a membrane 34 that is suspended on a silicon substrate 36. A Lorentz force is created by the interaction of the alternating surface current I flowing in the current conductor lines 32 and the in-plane static magnetic field B perpendicular to the current flow direction, according to the right-hand rule. Preferential coupling to a particular membrane mode is achieved by positioning the current lines 32 along antinodes of the longitudinal mode. When the alternating current I has the natural frequency of the mag-FPW resonator 30, a large amplitude standing wave is set up in the membrane wave plate 34. The motion of the current lines 32 in the magnetic field B in turn induces a back electromotive force (back-emf) opposing the motion. This back-emf is electrically manifested as an increase in impedance of the current lines 32 that can be detected at the membrane resonances.

In vacuum, membrane resonances are excited at angular resonant frequencies given by $$\omega_{mn} = k_{mn}\left(\frac{Dk_{mn}^2 + T}{\rho_s}\right)^{1/2}$$

where $k_{mn}$ is the wavenumber, $D=Eh^3/[12(1-\upsilon^2)]$ is the membrane bending moment, T tension (force per edge length), $\rho_s$ is the areal mass density, E is Young's modulus, $\upsilon$ is Poisson's ratio, and h is the membrane thickness.

Because the waves are excited in a bounded membrane that acts as a resonant cavity, the mag-FPW resonator can have a high quality factor, Q, with a narrow-band response. The high-Q results in a large vibration amplitude for a given input power and good frequency stability. The Q-factor of such a mag-FPW resonator under vacuum conditions is sufficient to enable high fidelity spectral analysis.

The mag-FPW resonator tested by Martin et al. had a 2-$\mu$m thickness, rectangular silicon nitride membrane with a meander-line transducer current line with electrodes positioned at the membrane antinodes. A resonant frequency of 263 kHz was obtained for a device with a meander-line periodicity of 400 $\mu$m. In vacuum, the Q-factor of this mag-FPW resonator was greater than several thousand.

For the micro acoustic spectrum analyzer of the present invention, a smaller mag-FPW resonator with a lower resonant frequency is preferred. The size and the frequency of the mag-FPW resonator can be reduced by reducing the thickness and tensile stress of the membrane. Typical membrane materials include low-stress amorphous diamond-like carbon, low-stress silicon nitride, and polymer films.

Figure 4:
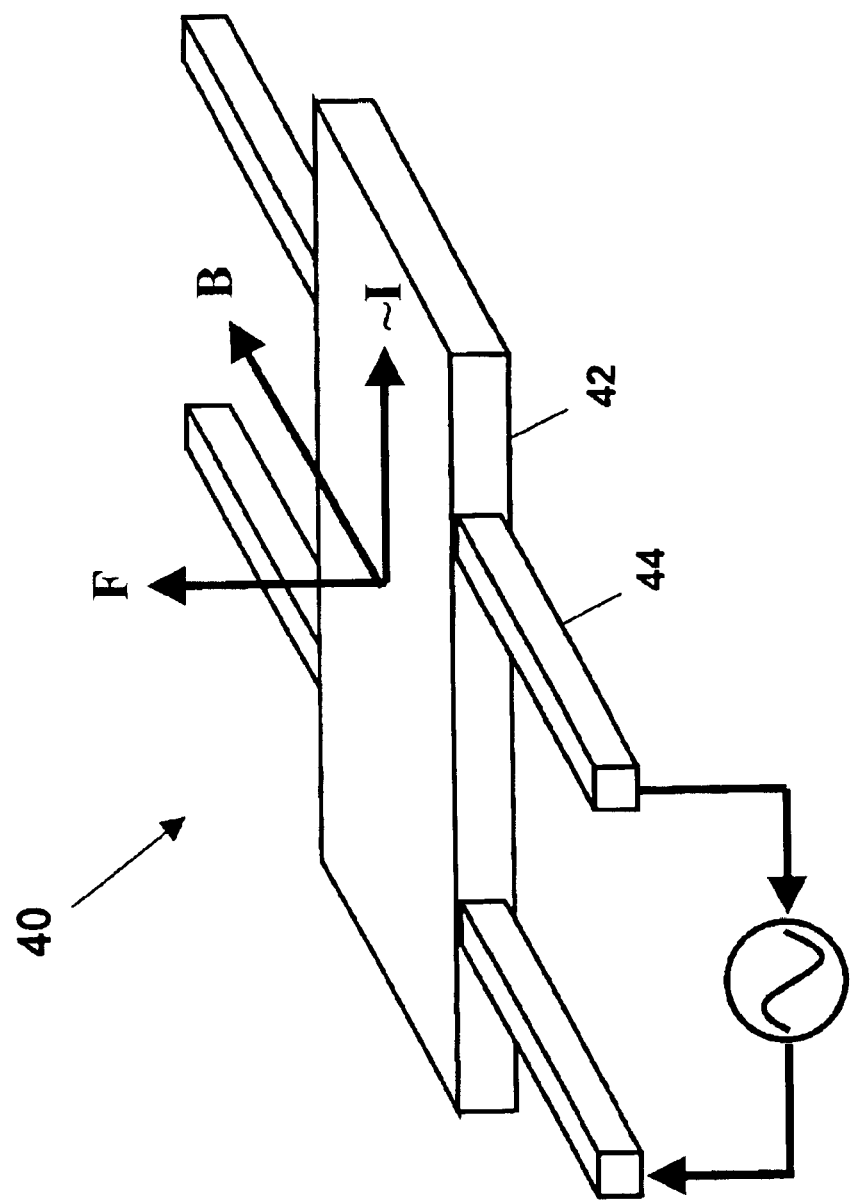
FIG. 4 shows a xylophone bar resonator.

Another electromagnetic resonator suitable for the present invention is a surface microfabricated xylophone bar resonator 40, illustrated schematically in FIG. 4. A magnetometer based on the xylophone resonator 40 is described in R. B. Givens et al., "A high sensitivity, wide dynamic range magnetometer designed on a xylophone resonator," *Appl. Phys. Lett.* 69(18), 2755 (1996) and D. K. Wickenden et al., "Micromachined polysilicon resonating xylophone bar magnetometer," *Acta Astronautica* 52, 421 (2003), which are incorporated herein by reference. This device is based on the classical resonating xylophone bar, but scaled down to a small size. The resonator element in this technology is simply a supported beam 42, rather than a membrane under tension. A xylophone bar magnetometer operates by using the Lorentz force F to transduce current flow I through the bar 42 crossing a magnetic field B into a mechanical force, which results in displacement of the bar 42. Two wires 44 can be placed at the nodal points of the fundamental mechanical resonance frequency of the xylophone bar 42. An oscillating Lorentz force F at the natural frequency of the beam 42 will drive it into a large amplitude bending mode.

The fundamental mechanical resonant frequency of xylophone-based resonator is $$\omega_0 = 22.4\sqrt{\frac{EI_a}{wl_b^4}} = \frac{2\pi 1.029b}{l_b^2}\sqrt{\frac{E}{\rho}}$$

where E is Young's modulus (N/m²), $l_b$ is the beam length (m), $I_B=ab^3/12$ is the area moment of inertia, w is the uniform load per unit length (=$\rho$ab), $\rho$ is the bar's density, $\alpha$ is the bar's length, and b is the bar's thickness. The deflection amplitude at the fundamental frequency is linearly proportional to the drive current I, magnetic field B, and the quality factor Q of the resonator. The Q-factor is determined by the bar's material parameters, such as ductility, and construction factors, such as the placement and width of the supports. The xylophone-based resonator can operate at lower magnetic fields than the mag-FPW resonator (e.g., 100 Gauss rather than 3–4 kGa), because the bar is free standing and undergoes large displacements, compared to the mag-FPW membrane which is under tension. Additionally, the xylophone resonator can have a high Q-factor, even when operated at atmospheric pressure.

The xylophone resonator can be fabricated on a silicon wafer using surface micromachining or other micromachining techniques. The xylophone bar can be made from a variety of materials, including silicon nitride, polysilicon, and amorphous diamond-like carbon. Typical xylophone bar dimensions are about 500-$\mu$m length, 50-$\mu$m width, and 1-$\mu$m thickness. Xylophone resonators having these dimensions have fundamental frequencies of between 50 and 100 kHz.

Figure 5:
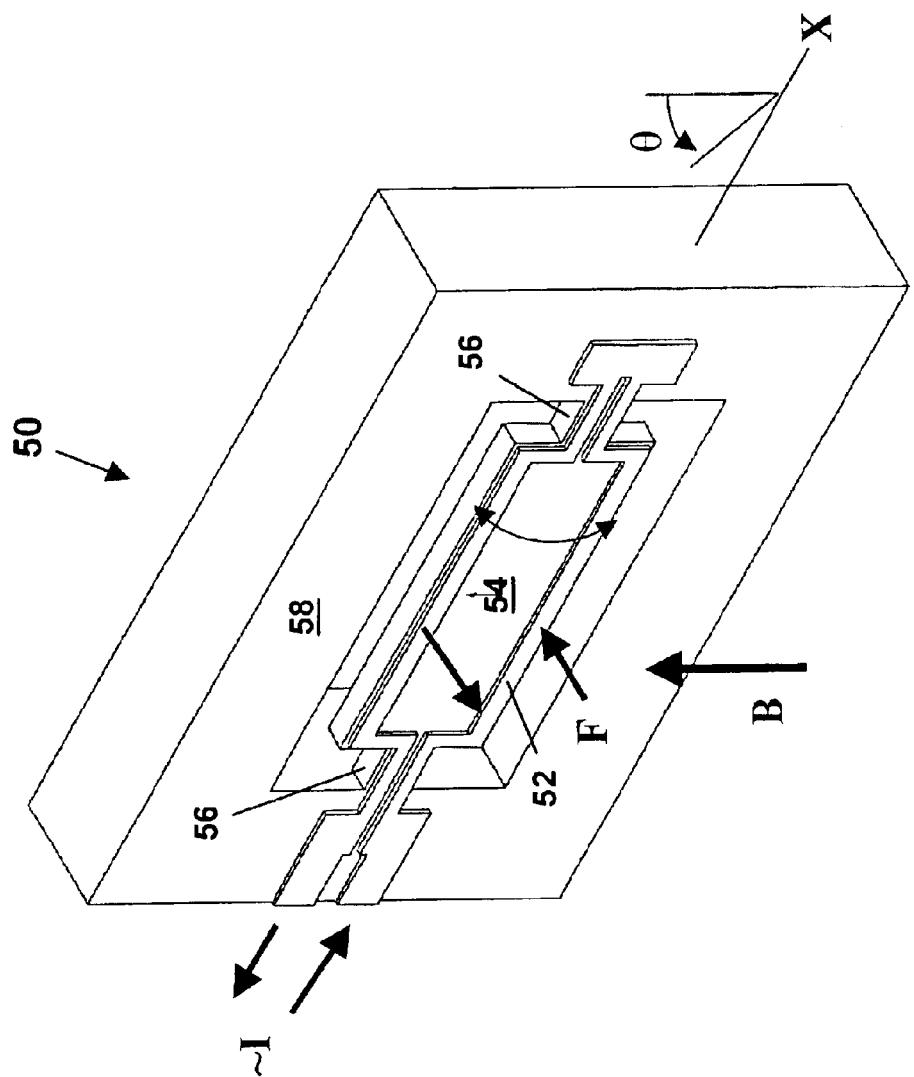
FIG. 5 shows a teeter-totter resonator.

Another electromagnetic resonator suitable for the present invention is the microfabricated teeter-totter resonator 50, illustrated schematically in FIG. 5. A teeter-totter resonator 50 is described in the co-pending U.S. patent application Ser. No. 10/436,597 to Adkins et al., which is incorporated herein by reference. The teeter-totter resonator 50 relies on the Lorentz force F to excite a torsional oscillation in a paddle 54. A current conductor line 52 runs along the perimeter of the paddle 54 that pivots about pivot arms 56 on each end of the paddle 54. The paddle 54 can be an insulating thin plate, which is typically silicon nitride, silicon dioxide, polysilicon, or a polymer. The paddle 54 is preferably rectangular in shape, although other shapes can also be used. The pivot arms 56 are pivotably connected to a frame 58. The frame 58 is typically silicon. The pivot arms 56 therefore define an axis of rotation X in the plane of the paddle 54. The rotational axis X is preferably the longitudinal axis of the rectangular paddle 54.

Permanent magnets (not shown) impose a static magnetic field B in the plane of the paddle 54. The source of the magnetic field B can be a conventional permanent magnet, direct-current (DC) coils, or the like. The magnetic field B is aligned substantially parallel to the plane of the paddle 54 and substantially perpendicular to the rotational axis X and the current direction in the conductor line 52. As shown in FIG. 5, application of an electrical current I to the conductor line 52 generates a surface-normal Lorentz force F directed according to the right-hand rule. Furthermore, because of the static B field, an alternating electrical current I through the conductor line 52 generates a reversing direction of the Lorentz force F on the paddle 54, causing the paddle 54 to oscillate from its rest position about the rotational axis X. The motion of the current conductor line in the magnetic field induces a back-emf in the conductor line opposing the motion that can be conveniently detected as a change in impedance of the current conductor line. In a one-port device, the excitation and detection of the oscillation of the teeter-totter resonator and its resonant frequency can be obtained directly through the ratio of the drive voltage to the drive current. Alternatively, in a two-port device, a second conductor line (not shown) can be run in a different region of the paddle (e.g., on the back side of the paddle) and the oscillation excited by the first conductor line can be detected as an output voltage in the second conductor line.

At a certain frequency, a resonant mode is established and the paddle undergoes maximum oscillations. The resonant frequency for the teeter-tooter resonator is given by $$\omega_n = \sqrt{k/J}$$

where $J=\rho wcL(c^2+w^2)/12$ is the polar moment of inertia of the paddle cross-section about the rotational axis, and $k=2\beta bc^3 G/a$ is the torsional spring constant of the pivot arms. The rectangular paddle has a width w, length L, thickness c, and effective density $\rho$. The pivot arms have a length a and width b. G is the shear modulus of elasticity of the pivot arm material and $\beta$ is approximately ⅓. Changing the cross-section or length of the pivot arms or the dimensions or mass of the oscillating paddle will alter the resonant frequency. For a silicon resonator paddle that is 0.6-mm wide, 10-$\mu$m thick, and 1.5-mm long, the resonant frequency is about 25 kHz. Such a teeter-totter resonator has a Q of about 1000 in vacuum.

The discussion of the micro acoustic spectrum analyzer has so far concentrated on using pre-selected, fixed tuned resonators across a frequency range of interest. Typically, the resonant frequency and Q-factor are fixed by the mechanical properties of the resonator. However, the micro acoustic spectrum analyzer can also use electronically tunable resonators whose resonant frequency and bandwidth (i.e., O-factor) can be adjusted electrically to track the spectral characteristics of the sound source "on the fly," as may be needed in a field application. In addition, the capability of active tuning allows correction on manufacturing variations, thereby enabling precise tuning to a narrow-band frequency of each resonator in an array. Such tunable resonators are described, for example, in U.S. Pat. No. 5,640,133 to MacDonald et al., U.S. Pat. No. 5,729,075 to Strain, U.S. Pat. No. 6,236,281 to Nguyen et al., U.S. Pat. No. 6,404,304 to Kwon et al., and the co-pending U.S. patent application Ser. No. 10/443,951 to Stalford et al., which are incorporated herein by reference.

Typically, the tunable resonator comprises a mechanical element (i.e., a supported beam or membrane) that is the "movable plate" of a capacitor structure that can be used to pull down on the mechanical resonator element in a controlled way so as to vary its resonant frequency and Q-factor. A RC or LRC capacitor-based circuit can provide feedback control coupled to the dynamics of the capacitor structure for tuning the bandwidth and resonant frequency response of the mechanical resonator. According to the method of Stalford et al., the capacitor-based circuit with a load resistor and voltage source is coupled to the mechanical resonator. The load resistor provides a loss mechanism for increasing the bandwidth of the resonator. The voltage source produces an attractive force between the movable plate and a fixed plate electrode that pulls the movable plate closer to the fixed plate, depending on the effective spring constant of the mechanical element, the initial separation distance, and the initial capacitance across the plates. For sufficiently large values of the load resistor and appropriate values of the capacitance and applied voltage, the bandwidth of the resonator can be increased by more than an order of magnitude while without changing the resonant frequency. Alternatively, by using a capacitor-based circuit with a self-inductance, the bandwidth can be increased while independently tuning the resonant frequency up or done by several percent, as compared to the natural frequency of the mechanical resonator.

Regardless of the type of resonator used in the micro acoustic spectrum analyzer, a vibration is set up in the resonator at the resonant excitation frequency. This vibration can be detected using a current-viewing resistor, capacitance, optical, or other means by the detector. The mag-FPW and teeter-totter resonators display an impedance change at resonance that can be easily detected with a bridge circuit. Signal conditioning electronics can amplify and rectify the bridge output resulting from the impedance change. The rectified signal can be converted by an RMS to DC converter to a DC voltage that is proportional to the effective average of the sound signal in the frequency bandwidth of the resonator filter. The vibrations of the xylophone resonator can be conveniently detected optically, or by using capacitive pick-off plates below the bar.

Tests with a Single Mag-FPW Resonator

Figure 6:
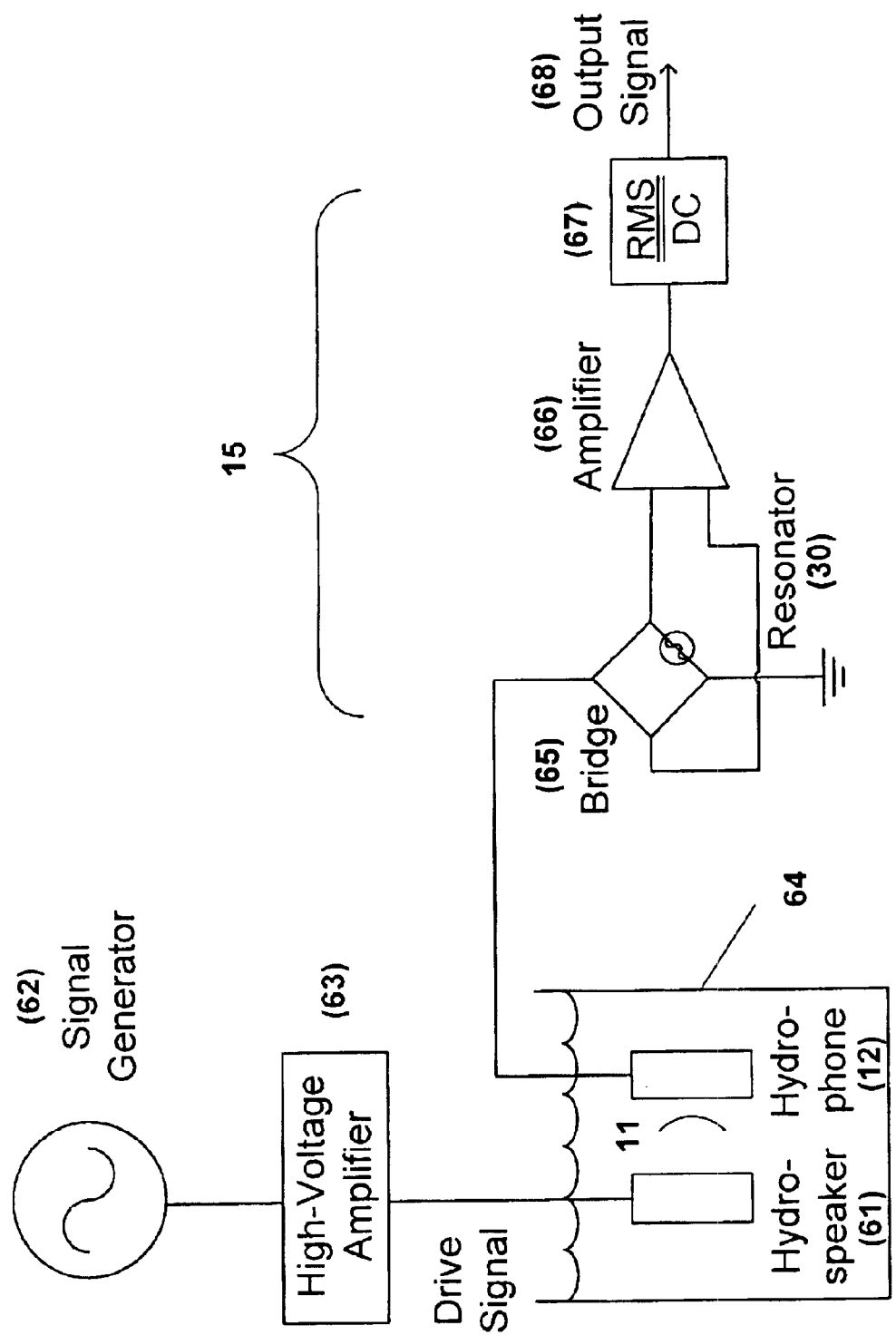
FIG. 6 shows a schematic illustration of a hydrospeaker test arrangement with a single mag-FPW resonator.

A series of tests were performed to verify that a single resonator could selectively filter frequency components from an underwater sound signal. In FIG. 6 is shown a schematic illustration of the hydrospeaker test arrangement with a single mag-FPW resonator 30. The mag-FPW resonator 30 was actuated with a low current to avoid causing inelastic deformations in the membrane.

To create a high frequency pressure wave 11 in the water, a hydrospeaker 61 was driven with a high-voltage sine wave. A mixer was not used for these tests, because the frequency of the sound signal from the hydrospeaker 61 could be matched to the resonant frequency of the mag-FPW resonator 30. The drive voltage for the hydrospeaker 61 was generated by coupling a signal generator 62 (e.g., an Agilent waveform generator) to a high-voltage amplifier 63. The hydrospeaker 61 and a pick up hydrophone 12 (i.e., the underwater analog of a microphone) were separated by 1.4 inches and submerged in a small bucket of water 64 for the tests. The hydrophone 12 used was a 1–3 piezocomposite hydrophone manufactured by Material Systems Inc. in Littleton, Mass. This hydrophone's resonant frequency of 500 kHz is well above the region of interest for the input pressure signal 11. The capacitance of the hydrophone is 500 pF and its audio gain is on the order of −185 dB based on a 1 V/$\mu$Pa reference. This gain implies that a 1-Pa pressure load gives a 562 $\mu$V signal.

The detector 15 for these tests comprised a single-active-element Wheatstone bridge 65 to measure the impedance change of the mag-FPW resonator 30, an operational amplifier 66 to amplify the bridge voltage, and an RMS-to-DC converter 67 to convert the amplifier AC output to a DC output voltage 68. The single mag-FPW resonator 30 formed the active leg of the bridge circuit for these tests. Therefore, the bridge output voltage is proportional to the relative change of the resonator's impedance. When the mag-FPW resonator 30 was not operating at resonance, the bridge 65 was balanced and the differential output from the bridge 65 was zero. At resonance, the mag-FPW resonator's impedance could more than double. At resonance, the voltage signal from the unbalanced bridge was amplified by the operational amplifier 66 and converted from a sine wave to a DC output signal 68 by the RMS-to-DC converter 67. The output signal 68 therefore is proportional to the intensity of the underwater sound signal 11 in the frequency band passed by the mag-FPW resonator 30.

Figure 7:
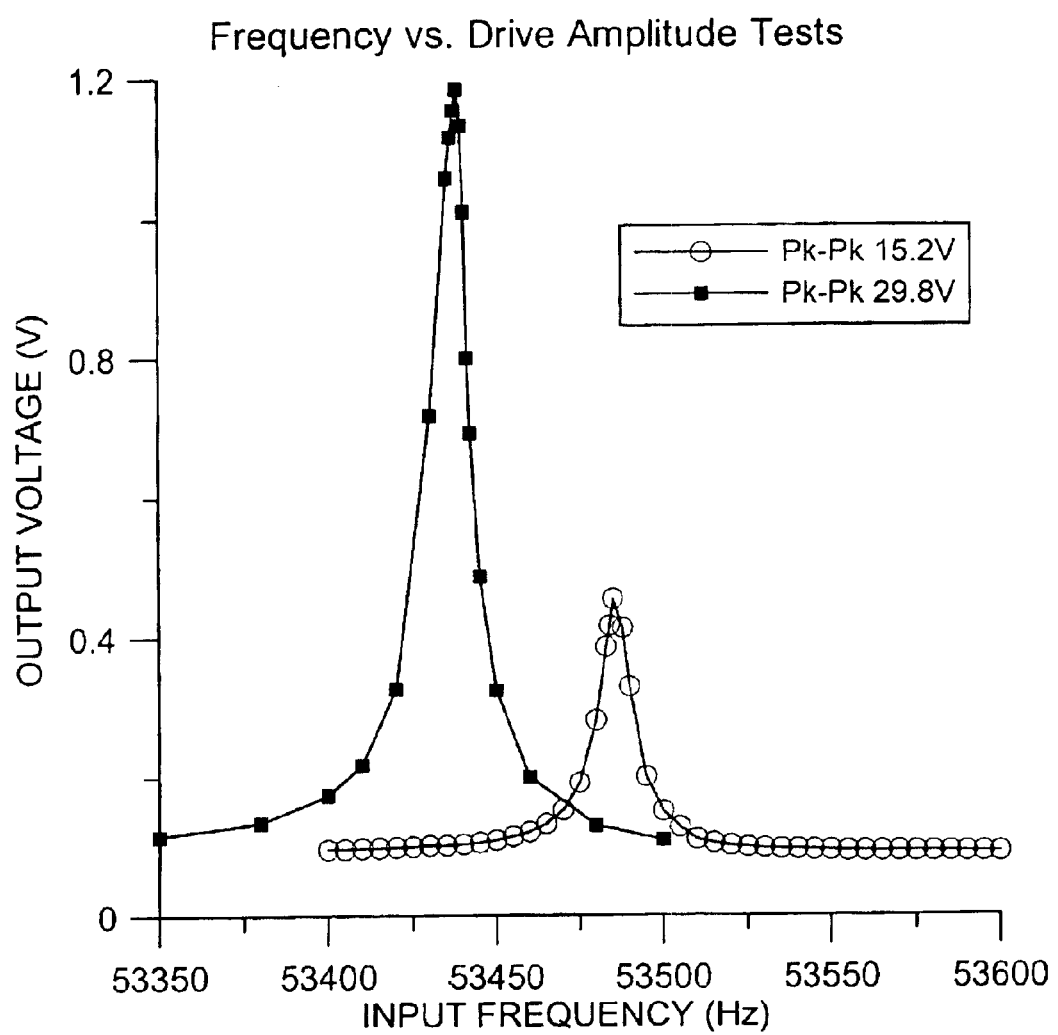
FIG. 7 shows the output signal of the mag-FPW resonator as the hydrospeaker frequency is swept across the resonant frequency.

In FIG. 7 is shown the output signal of the RMS-to-DC converter as the hydrospeaker drive voltage is swept across the mag-FPW resonator's resonant frequency. Shown are the results for two AC drive voltage amplitudes: 15.2 V peak-to-peak and 29.8 V peak-to-peak. The bandwidth is on the order of 20 Hz (i.e., Q of about 2700) for both drive voltages.

The resonant peak moved by about 50 Hz from one test voltage to the next. This drift in the resonant peak is most likely caused by temperature changes in the membrane of the mag-FPW resonator between the two tests. Typically, the resonant peak of a mag-FPW resonator drifts about 1 kHz per degree C. The teeter-totter resonator shown in FIG. 5 has a drift of only about 2 Hz per degree C. and would significantly reduce the temperature drift. Alternatively, the mag-FPW resonator could be enclosed in a temperature-controlled environment.

Tests with a Bank of mag-FPW Resonators

Figure 8:
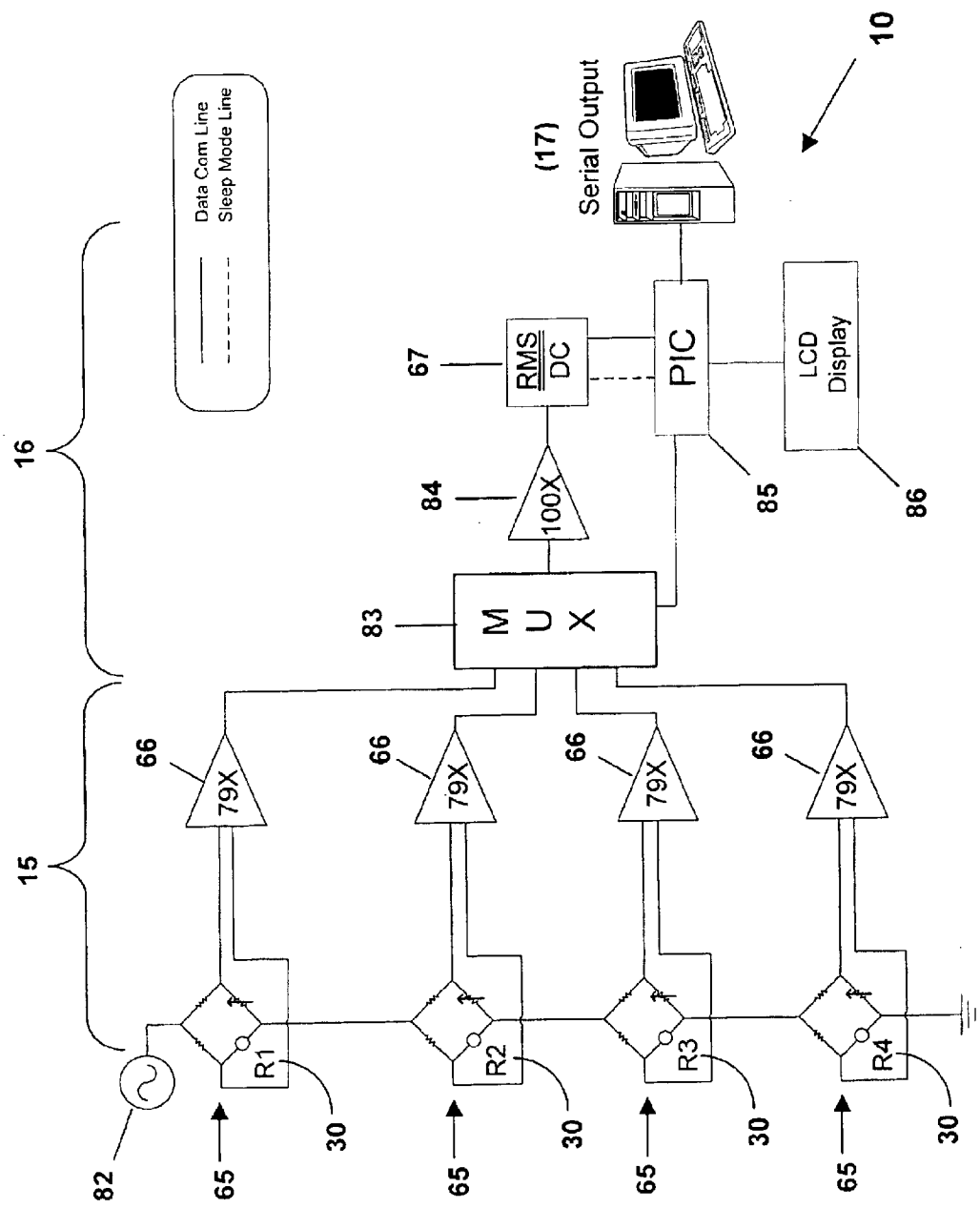
FIG. 8 shows a schematic illustration of a test arrangement comprising a parallel bank of mag-FPW resonators.

In FIG. 8 is shown a schematic illustration of a micro acoustic spectrum analyzer 10 that was used to identify multiple frequency components in a test signal. The micro acoustic spectrum analyzer 10 that was tested comprised a bank of mag-FPW resonators 30, a detector 15, a storage/scanning device 16, and a pattern recognition device 17. For these tests, rather than using a microphone 12 to convert a sound signal to an electrical signal, a waveform generator 82 was used to drive the bank of mag-FPW resonators 30.

The waveform generator 82 drove the resonator bridge circuit with a 4-mV peak-to-peak sinusoidal signal. The detector circuitry 15 for each mag-FPW resonator 30 comprised a Wheatstone bridge 65 and an operational amplifier 66. The four bridge circuits were connected in series with a mag-FPW resonator 30 in one leg of each bridge 65. The balanced output from each bridge 65 was amplified by the operational amplifier 66 to provide an AC signal with peak-to-peak voltage proportional to the drive signal in the frequency band passed by that mag-FPW resonator 30. The storage/scanning device 16 comprised a multiplexer (MUX) 83, a second-stage amplifier 84, an RMS-to-DC converter 67, and a programmable integrated circuit (PIC) 85. The AC signal from each operational amplifier 66 was sent to the single-chip MUX 83. The output of the MUX 83 was amplified by the second-stage amplifier 84 and then converted to a DC output signal by the RMS-to-DC converter 67. The PIC 85 switched between the channels of the MUX 83 and read the stored signals with its on-board 8-bit analog-to-digital converter (ADC). The output of the PIC 85 was then fed to a computer 87 for further analysis and to compare the signature of the scanned signals against a library of profiles. Alternatively, the output of the PIC 85 could be read out by an LCD display 86.

Figure 9:
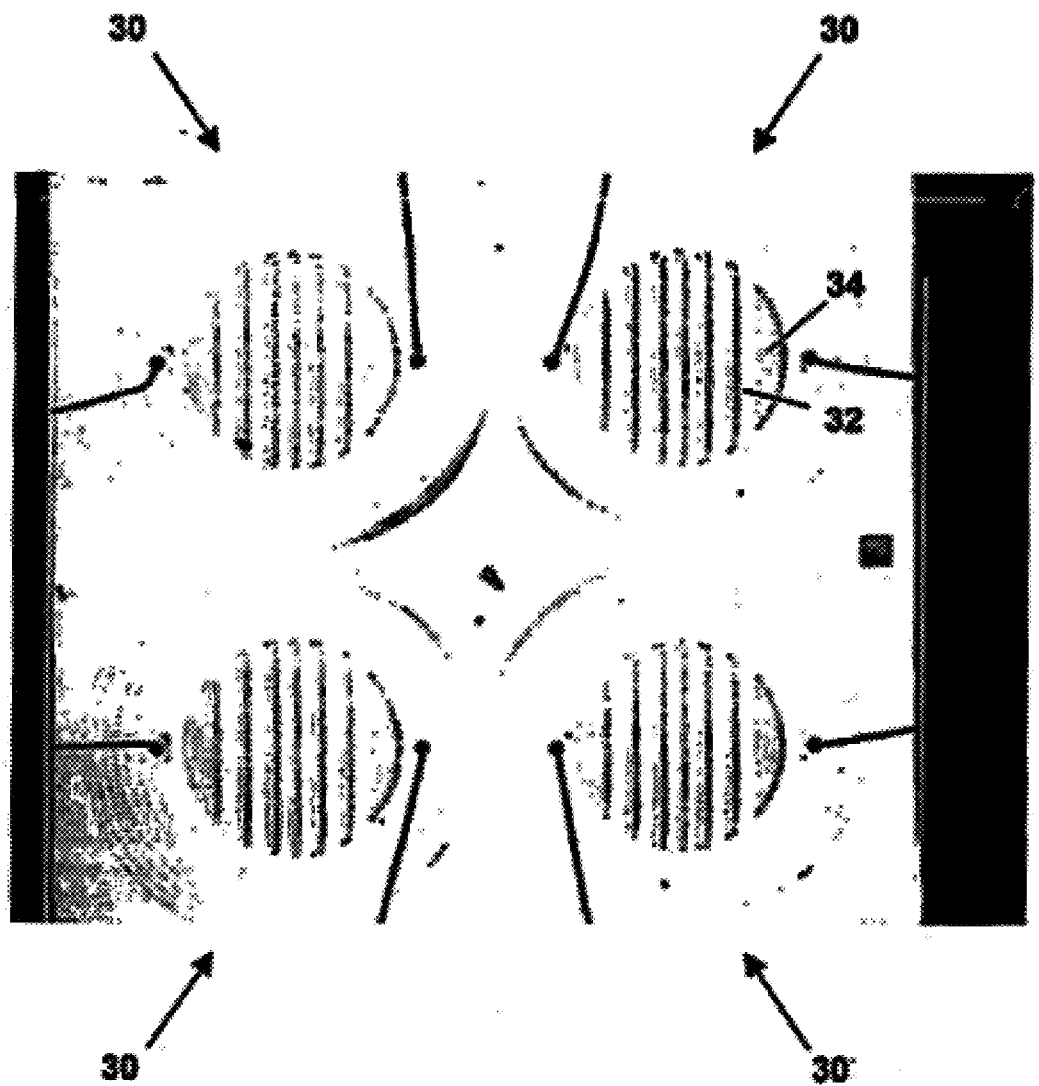
FIG. 9 shows an array of four mag-FPW resonators on a silicon chip.

In FIG. 9 is shown the array of four mag-FPW resonators 30 on a single silicon die used for these tests. Each mag-FPW resonator 30 had a circular "drumhead"-type membrane 34. The membrane material for these resonators was silicon nitride. Permanent magnets around the membranes 34 applied a magnetic flux in a direction perpendicular to the current conductor lines 32 that ran across the circular membrane 34. As an alternating current passed through the current lines 32, Lorentz forces applied a load to the membrane 34. At resonance, membrane displacements were large enough to produce a back-emf in the current lines 32 that increased the impedance of the mag-FPW resonator 30. This impedance change was picked up by its corresponding bridge. Four different membrane diameters were used to provide fundamental-mode resonances at four distinct frequencies. The resonator membrane was approximately 0.6 $\mu$m thick and the diameters ranged from 1.44 to 1.50 mm.

Figure 10:
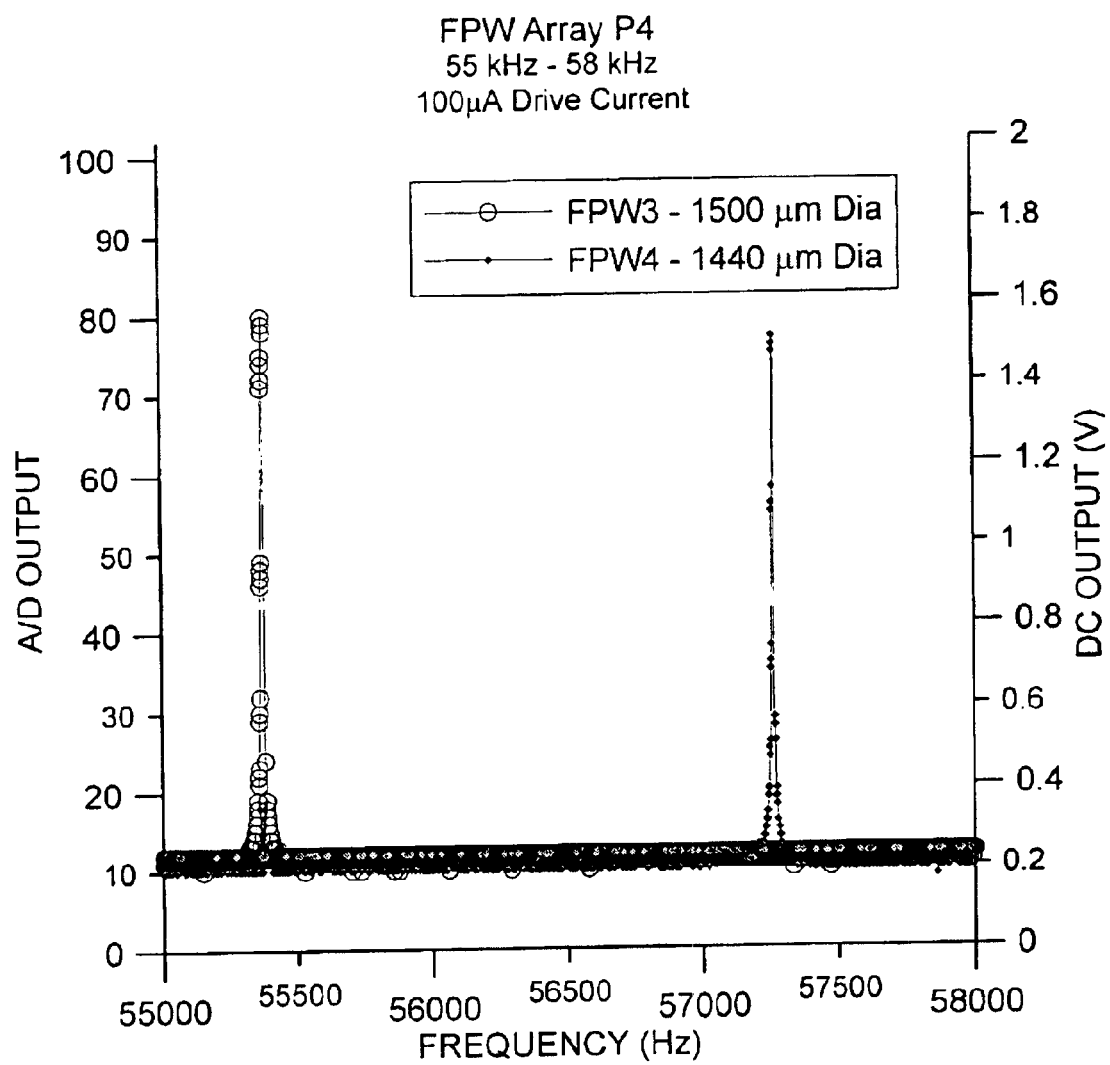
FIG. 10 shows the frequency response of two of the mag-FPW resonators as the input signal is swept across their resonant frequencies.

FIG. 10 shows the output of the ADC of the MUX as the frequency is changed. The PIC took data at a scanning rate of 13 samples per second per channel and transferred data over a serial line to the computer. The 1.50-mm mag-FPW resonator resonated at 55.4 kHz and the 1.44-mm mag-FPW resonator resonated at 57.2 kHz. The 4 mV drive voltage produced a signal of about 80 A/D counts from the ADC. The noise in this signal was about ±2 A/D counts or about ±40 mV on the 8-bit converter. Since the computer read the signal directly, it could easily perform a comparison of the signal strength of each channel to one or more profiles from a library. If the relative magnitude in each spectrum matched with a profile, the computer sent out an alarm.

The micro acoustic spectrum analyzer of the present invention can provide a low power, miniature system useful in applications were size, accessibility, and power availability are limited. With currently available components, the micro acoustic spectrum analyzer can have a steady state power consumption of about 70 mW. If samples are only needed every 100 seconds, then the micro acoustic spectrum analyzer could be operated in a sleep mode such that the PIC could wake up the system, gather data for 1 second, perform the profile comparison, and return to power-down mode. This sleep mode operation could reduce power consumption by about two orders of magnitude. The micro acoustic spectrum analyzer used for these tests had surface mount components and occupied a volume of about 24 cubic inches. The electronics and the permanent magnets could be moved into a 2 cubic inch package with a system redesign.

The present invention has been described as micro acoustic spectrum analyzer. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A micro acoustic spectrum analyzer for determining the frequency components of a fluctuating sound signal, comprising:
   a microphone to pick up the fluctuating sound signal and produce an alternating current electrical signal;
   at least one microfabricated resonator, each resonator having a different resonant frequency, that vibrates in response to the alternating current electrical signal; and
   at least one detector to detect the vibration of the at least one microfabricated resonator.

2. The micro acoustic spectrum analyzer of claim 1, further comprising a mixer to mix a reference signal with the alternating current electrical signal from the microphone to shift the frequency spectrum of the alternating current electrical signal to a frequency range that is a better matched to the resonant frequencies of the at least one microfabricated resonator.

3. The micro acoustic spectrum analyzer of claim 1, further comprising means for storing and scanning the detected vibrations from each of the at least one detector.

4. The micro acoustic spectrum analyzer of claim 1, further comprising a pattern recognition processor to compare the detected vibrations from the at least one detector to a library of profiles.

5. The micro acoustic spectrum analyzer of claim 1, wherein the microphone comprises a hydrophone.

6. The micro acoustic spectrum analyzer of claim 1, wherein the at least one microfabricated resonator comprises silicon-based materials.

7. The micro acoustic spectrum analyzer of claim 1, wherein the resonant frequency of the at least one microfabricated resonator is greater than 20 kHz.

8. The micro acoustic spectrum analyzer of claim 1, wherein the at least one microfabricated resonator comprises an electromagnetic resonator.

9. The micro acoustic spectrum analyzer of claim 8, wherein the electromagnetic resonator comprises a flexural plate wave resonator.

10. The micro acoustic spectrum analyzer of claim 8, wherein the electromagnetic resonator comprises a teeter-totter resonator.

11. The micro acoustic spectrum analyzer of claim 8, wherein the electromagnetic resonator comprises a xylophone resonator.

12. The micro acoustic spectrum analyzer of claim 1, wherein the at least one microfabricated resonator comprises a tunable resonator having a resonant frequency and a bandwidth that can be adjusted electrically.

13. The micro acoustic spectrum analyzer of claim 12, wherein the electrical adjustment comprises a capacitor-based circuit.

14. The micro acoustic spectrum analyzer of claim 1, wherein the at least one detector is selected from the group consisting of a current-viewing resistor, capacitance means, and optical means.

* * * * *